(12) United States Patent
Bateman et al.

(10) Patent No.: US 7,326,578 B2
(45) Date of Patent: Feb. 5, 2008

(54) URINE ASSAY FOR OVARIAN RESERVE

(75) Inventors: Paul North Bateman, Kingston-Upon-Thames (GB); Simon John Rattle, Kingston-Upon-Thames (GB)

(73) Assignee: Genosis (UK) Limited, Surrey (GB)

( * ) Notice: Subject to any disclaimer, the term of this patent is extended or adjusted under 35 U.S.C. 154(b) by 591 days.

(21) Appl. No.: 10/470,728

(22) PCT Filed: Feb. 14, 2002

(86) PCT No.: PCT/GB02/00623

§ 371 (c)(1),
(2), (4) Date: Aug. 26, 2003

(87) PCT Pub. No.: WO02/065128

PCT Pub. Date: Aug. 22, 2002

(65) Prior Publication Data

US 2004/0063219 A1    Apr. 1, 2004

(30) Foreign Application Priority Data

Feb. 15, 2001    (GB) ................................ 0103755.5

(51) Int. Cl.
*G01N 33/53*    (2006.01)
(52) U.S. Cl. .................... 436/514; 436/7.92; 436/7.93; 436/7.94; 436/7.5; 436/531; 436/533; 436/805; 436/808; 436/810; 435/287.1; 435/287.2; 435/287.9; 435/805; 435/810; 435/969; 435/970; 435/973
(58) Field of Classification Search ................ 435/514, 435/7.92, 7.93, 7.94, 7.5, 287.1, 287.2, 287.9, 435/805, 810, 969, 970, 973, 975; 436/169, 436/518, 531, 533, 805, 808, 810
See application file for complete search history.

(56) References Cited

U.S. PATENT DOCUMENTS 6,924,153 B1 *   8/2005   Boehringer et al. ........ 436/514

FOREIGN PATENT DOCUMENTS

| EP | 0 736 771 | 10/1996 |
| WO | WO 96/09553 | * 3/1996 |

(Continued)

OTHER PUBLICATIONS

G. J. E. Oosterhuis et al., "Follicle Stimulating Hormone Measured in Urine: A Possible Tool to Testing Ovarian Reserve", Clinical Chemistry, vol. 44, No. 6, 1998, p. A148, XP001120132, Abstract.

(Continued)

*Primary Examiner*—Bao-Thuy L. Nguyen
(74) *Attorney, Agent, or Firm*—Wenderoth, Lind & Ponack, L.L.P.

(57) ABSTRACT

It has been found that a urine test for ovarian reserve can be provided which is equivalent in sensitivity to current laboratory methods which determine ovarian reserve based on FSH levels in serum. A lateral flow device for indicating ovarian reserve is disclosed. The device has an application zone for receiving a urine sample, a labelling zone containing label which binds to FSH in the sample, and a detection zone where FSH-bound label is retained. The detection zone has a threshold value which corresponds to a serum FSH level of between 5-20 mIU/ml (e.g. 10 mIU/ml). A test result above the threshold value indicates diminished ovarian reserve.

20 Claims, 1 Drawing Sheet

FOREIGN PATENT DOCUMENTS

| | | |
|---|---|---|
| WO | 98 22824 | 5/1998 |
| WO | 98 39657 | 9/1998 |

OTHER PUBLICATIONS

G. J. E. Oosterhuis et al., "Follicle-Stimulating Hormone Measured in Unextracted Urine: A Reliable Tool for Easy Assessment of Ovarian Capacity", Fertility and Sterility, vol. 70, No. 3, 1998, pp. 544-548, XP002220704, Abstract.

G. J. E. Oosterhuis et al., "Assessment of Ovarian Reserve", Journal of Clinical Ligand Assay, vol. 20, No. 4, 1997, XP009000606, p. 321, Abstract.

S. W. Trout et al., "Do Women with Unexplained Recurrent Pregnancy Loss have Higher Day 3 Serum FSH and Estradiol Values?", Fertility and Sterility, vol. 74, No. 2, 2000, pp. 335-337, XP002220705, p. 336.

UK Scientists Develop, "His-and-Hers" Fertility Test Kit, Online, Jul. 4, 2001.

* cited by examiner

URINE ASSAY FOR OVARIAN RESERVE

This application is a U.S. national stage of International Application No. PCT/GB02/00623 filed Feb. 14, 2002.

All documents cited herein are hereby incorporated by reference in their entirety.

TECHNICAL FIELD

This invention relates to assays for testing ovarian reserve in pre-menopausal women.

BACKGROUND ART

Diminished ovarian reserve generally reflects the processes of follicular depletion and decline in oocyte quality, and a female with diminished ovarian reserve has a greatly reduced chance of conceiving.

It is known that the level of follicle stimulating hormone (FSH) in blood measured at day 3 of the menstrual cycle is a good predictor of ovarian reserve. Whilst serum tests are the "gold standard", they are not suited to home use and, for convenience, urine tests would be preferable.

Urinary tests for FSH are commercially available (e.g. the Serono Maiaclone FSH test, Amersham Amerlex FSH test), but these tests have several disadvantages.

The Serono and Amersham tests both require the collection of timed urine samples (typically two samples passed 3 hours apart) and must be calibrated to take account of the total sample volume in order to give a result in terms of quantity of FSH per hour. The need to measure urine volume (equivalent to dilution) and the uncertainty of knowing the accuracy of the 3 hour timed interval between voids are clear disadvantages.

As an alternative to compensating for the time interval between voids, tests are available which work on random urine specimens. These tests require measurement of creatinine concentration in a specimen, however, and calculate the result in terms of the ratio of quantity of FSH to quantity of creatinine. In this case, a disadvantage is the requirement to measure the creatinine concentration as well as the FSH concentration.

Tests are available which measure urine FSH levels directly, but these suffer from technical difficulties in terms of ovarian reserve measurements. The tests are designed for indicating the onset of the menopause and give a yes/no indication based on a threshold value of 25 mIU/ml (standardised against the WHO Second International Standard IS 80/552) but it has been found by the present inventors that this threshold value is too high for measuring ovarian reserve.

It is an object of the present invention to provide assays which can distinguish between normal and diminished ovarian reserve based on urine samples. It is a further object to provide such tests which allow direct measurement from urine, which avoid complex calibration steps, and which are suited to home use. In particular, it is an object to provide tests which avoid pre-treatment of the specimen, the need for accurate timing, comparisons with standard creatinine concentrations, or volume measurement.

DISCLOSURE OF THE INVENTION

Surprisingly, it has been found that a yes/no urine test for ovarian reserve can be provided which is equivalent in sensitivity to current laboratory methods based on serum FSH levels. Moreover, the test can be achieved without the need for adjustments in order to take account of timing, dilution, creatinine concentration etc.

The invention provides a lateral flow device for indicating ovarian reserve. The device has an application zone for receiving a urine sample, a labelling zone containing label which binds to FSH in the sample, and a detection zone where FSH-bound label is retained.

Label retained in the detection zone gives a signal, and the signal differs depending on whether FSH levels are lower than or equal to/greater than a given threshold concentration. In the device of the invention, this threshold concentration represents a serum FSH concentration of between 5 mIU/ml and 20 mIU/ml, preferably between 8 mIU/ml and 12 mIU/ml, and most preferably approximately 10 mIU/ml.

In preferred devices, therefore, the signal given for a sample from patients with a serum FSH level lower than 10 mIU/ml (satisfactory ovarian reserve and egg quality) is different from the signal given for a sample from patients with a serum FSH level equal to or greater than 10 mIU/ml (associated with diminished ovarian reserve and poor egg quality). For measuring ovarian reserve, recent studies investigating an appropriate cut-off level for serum FSH levels suggest using a lower level than used historically [e.g. Trout & Seifer (2000) *Fertility and Sterility* 74(2):335-7; Ahmed Ebbiary et al. (1994) *Human Reproduction* 9:245-52]. Based on these data, the current standard for tests that use FSH levels to predict fertility problems is to use a cut-off value of 10 mIU/mL [Trout & Seifer supra]. Thus, whilst some workers have used thresholds of basal FSH levels as high as 40 mIU/mL [e.g. Goldenberg et al. (1973) *American Journal of Obstetetrics and Gynecology* 116:1003; Fauser et al. (1986) Geburtsh Frauenheilkd 46: 735], more recent work with currently available WHO IRP standards and immunometric assay technology focuses on lower values, and figures of 10-15 mIU/mL are now widely supported as thresholds for declining ovarian reserve [e.g. Seifer et al. (1996) *Fertility and Sterility* 66:593-8; Scott et al. (1989) *Fertility and Sterility* 51:6514; Toner et al. (1991) *Fertility and Sterility* 55:784-91; Ahmed Ebbiary et al. supra].

In the following discussion, a urine sample from a patient having a serum FSH level equal to the threshold concentration is referred to as a "threshold urine sample".

The principles and technology of lateral flow devices are well known, but specific aspects of the invention are set out in further detail below.

The application zone in the device is suitable for receiving a urine sample. It is typically formed from absorbent material such as blotting paper.

The labelling zone contains label which binds to any FSH in the urine sample. For reasons of specificity, the label is typically antibody. For ease of detection, the label is preferably visible to the naked eye e.g. it is tagged with a fluorescent tag or, preferably, a coloured tag such as conjugated colloidal gold, which is visible as a pink colour.

The detection zone retains FSH to which label has bound. This will typically be achieved using an immobilized capture reagent, such as an antibody. Where the capture reagent and the label are both antibodies, they will recognise different epitopes on the hormone (e.g. on different subunits). This allows the formation of a 'sandwich' comprising antibody-FSH-antibody.

The detection zone is downstream of the application zone, with the labelling zone typically located between the two. A urine sample will thus migrate from the application zone into the labelling zone, where any FSH in the sample binds to the label. FSH-label complexes continue to migrate into the detection zone together with excess label. When the FSH-label complex encounters the capture reagent, the complex is retained whilst the sample and excess label continue to migrate. As FSH levels in the sample increase, the amount of label (in the form of FSH-label complex) retained in the detection zone increases proportionally.

A key feature of the device of the invention is the ability to distinguish between samples according to the threshold concentration. This can be achieved in various ways.

One type of device includes a reference zone which includes a signal of fixed intensity against which the amount of label retained in the detection zone can be compared—when the signal in the detection zone equals the signal in the reference zone, the sample is a threshold urine sample; when the signal in the detection zone is less intense than the reference zone, the sample contains less FSH than a threshold urine sample; when the signal in the detection zone is more intense than the reference zone, the sample contains more FSH than a threshold urine sample. In a preferred device, therefore, the reference zone has a signal which is the same as the signal given in the detection zone for a sample from a patient with a serum FSH level of 10 mIU/ml. A suitable reference zone can be prepared and calibrated without difficulty. For this type of device, label will generally be present in excess to FSH in the urine sample, and the reference zone may be upstream or, preferably, downstream of the detection zone. It is apparent that the signal in the reference zone will be of the same type as the signal in the detection zone i.e. they will typically both be visible to the naked eye e.g. they will use the same tag. A preferred reference zone in a device of this type comprises immobilised protein (e.g. bovine serum albumin) which is tagged with colloidal gold.

In another device, the reference zone is downstream of the detection zone and includes a reagent which captures label (e.g. an immobilised anti-label antibody). Label which flows through the device is not present in excess, but is at a concentration such that 50% of it is bound by a sample having FSH at the threshold concentration. In a threshold urine sample, therefore, 50% of the label will be retained in the detection zone and 50% in the reference zone. If the FSH level in the sample is greater than in a threshold urine sample, less than 50% of the label will reach the reference zone and the detection zone will give a more intense signal than the reference zone; conversely, if the FSH level in the sample is less than in a threshold urine sample, less than 50% of the label will be retained in the detection zone and the reference zone will give a more intense signal than the detection zone.

In another device which operates according to similar principles, the reference zone is downstream of the detection zone and includes a limiting amount of a reagent which captures label (e.g. an immobilised anti-label antibody). The reagent is present at a level such that it retains the same amount of label which would bind to detection zone for a threshold urine sample, with excess label continuing to migrate beyond the reference zone.

In these three types of device, therefore, a comparison between the detection zone and the reference zone is used to compare the sample with the threshold concentration. The detection:reference binding ratio can preferably be determined by eye. Close juxtaposition of the detection and reference zones is preferred in order to facilitate visual comparison of the signal intensities in the two zones. This is typical in, for instance, ovulation predictor kits.

In a fourth type of device, no reference zone is needed, but the detection zone is configured such that it gives an essentially on/off response i.e. no signal is given below the threshold concentration but, at or above the threshold, signal is given.

In a fifth type of device, no reference zone is needed, but an external reference is used which corresponds to the threshold concentration. This can take various forms e.g. a printed card against which the signal in the detection zone can be compared, or a machine reader which compares an absolute value measured in the detection zone (e.g. a calorimetric signal) against a reference value stored in the machine.

In some embodiments of the invention, the device includes a control zone downstream of the detection zone. This will generally be used to capture excess label which passes through the detection and/or reference zones (e.g. using immobilised anti-label antibody). When label is retained at the control zone, this confirms that mobilisation of the label and migration through the device have both occurred. It will be appreciated that this function may be achieved by the reference zone.

The detection, reference and control zones are preferably formed on nitrocellulose.

Migration from the application zone to the detection zone will generally be assisted by a wick downstream of the detection zone to aid capillary movement. This wick is typically formed from absorbent material such as blotting or chromatography paper.

The device of the invention can be produced simply and cheaply, conveniently in the form of a dipstick. Furthermore, it can be used very easily, for instance by the home user. The invention thus provides a device which can be used at home as a screen of ovarian reserve.

The invention also provides a process for measuring ovarian reserve, comprising the steps of: (a) obtaining a urine sample from a female; (b) contacting the sample with a label which binds to any FSH in the sample; (c) separating FSH-bound label; (d) detecting a signal associated with the separated label from step (c); and (e) comparing the signal detected in step (d) with a reference signal which corresponds to the signal given by a urine sample from a patient with a serum FSH level equal to a threshold concentration, wherein said threshold concentration is between 5 mIU/ml and 20 mIU/ml. This process preferably utilises a device of the invention.

The urine sample applied to the device will usually be one obtained on day 3±1 of the menstrual cycle (a "day 3" sample). Samples from day 3 are preferred. [Hansen et al. (1997) Evaluating ovarian reserve: follicle stimulating hormone and oestradiol variability during cycle days 2-5. *Hum. Reprod.* 12:486-9]

To achieve diagnostic acceptability, the measurement of urinary FSH must minimise the concentration fluctuations that occur as a result of variations in fluid intake and in the time of taking the specimen since the last void. It has been found that first morning urine samples are advantageous for measuring PSH levels as (a) there is a more uniform time since the last void, typically between 6 and 8 hours, and (b) fluid intake does not occur during sleep. By minimising the variation in timing and in fluid intake, and effectively providing a specimen integrated over a longer period than the 3 hours used by the prior art tests, the need to compensate for volume or for creatinine concentration is avoided.

Accordingly, the urine sample applied to the device is preferably a first morning urine sample.

The term "first morning urine" means the first urine to be passed following a normal period of sleep (e.g. 6 to 8 hours).

These samples have been found to show good consistency of FSH concentrations and good correlation with serum FSH levels.

The use of first morning samples allows direct measurement of FSH levels, without pre-treatment of the specimen, without compensating for the dilution (or concentration) of the urine by adjusting the result in line with creatinine concentration, and without the need to measure the volume of the urine in order to present the result in terms of the quantity of FSH per hour.

There are currently no assays for direct measurement of FSH levels in urine which are suitable for determining ovarian reserve. For other female hormones (e.g. hCG, LH), assays are available that use direct measurement of urine without the need to measure the urine volume. In the case of the hCG tests, however, the quantity of hormone present in positive samples is high and the interpretation of results is not significantly affected by relatively large variations in concentration of the hormone. For the LH tests, the result is interpreted in relation to a major change of concentration on a day-to-day basis, not in relation to a particular concentration of the hormone. Neither of these tests suffer the same problems as FSH in needing to minimise fluctuations from variable fluid intake and variation in the timing of specimen, as their diagnostic decision levels are higher both in absolute terms and in relation to the concentration of hormone present in negative test conditions. The diagnostic decision level for FSH tests, however, is relatively low compared with the concentrations of other hormones that are measured in urine and hence there is an increased need to achieve consistency of the specimen, both between and within different individuals.

It will be appreciated that the term 'antibody' may include polyclonal and monoclonal antibodies, as well as antibody fragments (e.g. $F(ab)_2$, Fc etc.), single chain Fvs etc., provided that the necessary binding activity and biological specificity are retained.

MODES FOR CARRYING OUT THE INVENTION

A Test Device

Figure 1:
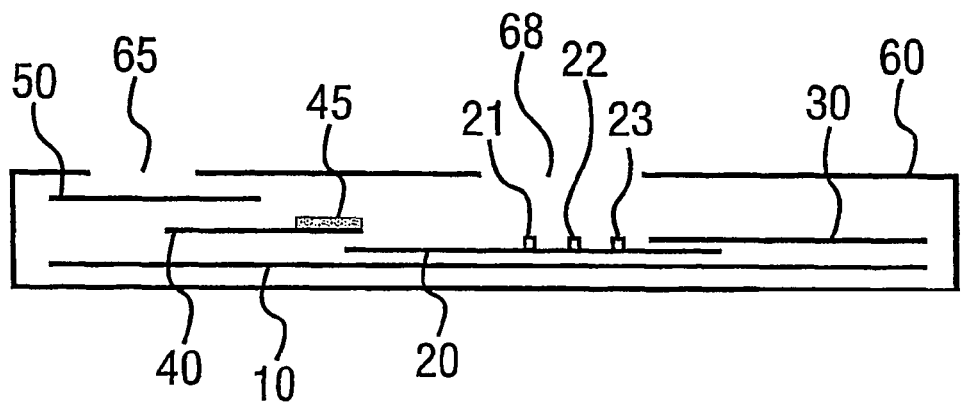
FIG. 1 shows the arrangement of strips in a device of the invention.
Figure 2:
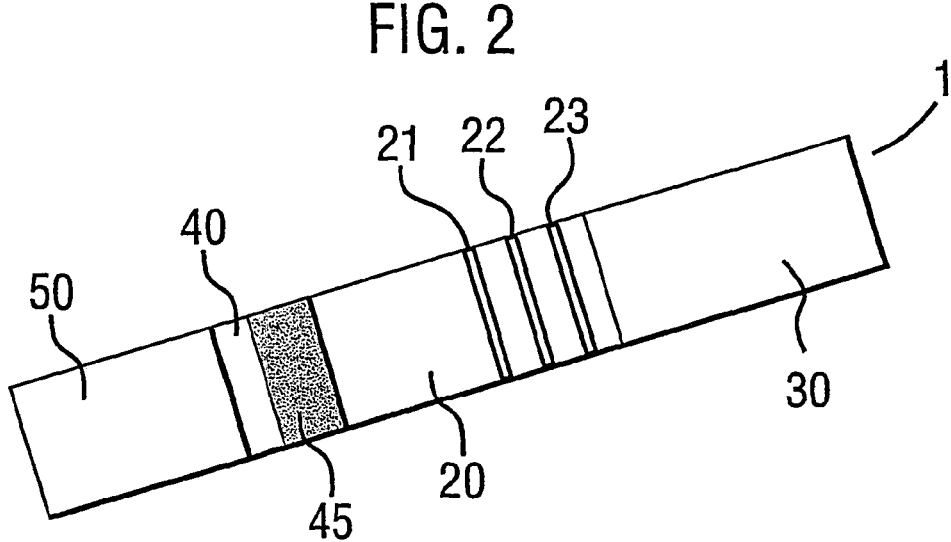
FIG. 2 shows a plan view of the assembled strips.

The test strip (1) of FIG. 2 was constructed on a plastic backing sheet (10) measuring 8 mm×59 mm, as shown in FIG. 1. A strip of nitrocellulose membrane (20) measuring 8 mm×25 mm (Millipore Corporation, Product Code HF135) was placed onto the backing sheet (10). An upper wick (30) measuring 8 mm×18 mm formed from blotting paper grade material (Ahlstrom Filtration, Product Code 222) was placed on top of the nitrocellulose at one end, with a partial overlap. At the other end, a polyester pad (40) measuring 8 mm×13 mm was placed over the nitrocellulose (20), and a piece of absorbent paper (50) measuring 8 mm×14 mm was placed on top of the pad (40). Paper (50) and pad (40) overlap by 6 mm.

Absorbent paper (50) was blotting paper grade material (Ahlstrom Filtration, Product Code 222; 14 mm×8 mm) that had been pre-soaked in 250 mM Tris, 0.5% Tween 20, pH 8.2, and then dried.

Polyester pad (40) was a polyester conjugate pad (Ahlstrom Filtration, Reemay Product Code 6615; 13 mm×8 mm) that has been pre-soaked in 250 mM Tris, 0.5% Tween 20, pH 8.2, and then dried. One end (45) was sprayed with colloidal gold (40 nm) conjugated to murine monoclonal anti-α FSH antibody (Medix Biochemica, Product Code 6601). 3 μl of OD10 gold conjugate was applied per test strip. To measure the concentration of gold particles in a given reagent sample, the conjugate under test is diluted to give an $OD_{520nm}$ of ~1.0, and this is multiplied by the dilution factor to give an equivalent OD for the original reagent sample.

The end (45) containing the antibody is not covered by paper (50) and overlaps nitrocellulose (20) by 1 mm.

The nitrocellulose strip (20) contains three stripes of immobilised antibody. The first stripe (21) is 11 mm downstream of area (45) and consists of monoclonal anti-β FSH (Medix Biochemica, Product Code 6602), applied by striping (1 μl/cm of 0.75 mg/ml antibody). The second stripe (22) is 14 mm downstream of area (45) and consists of colloidal gold (40 nm) conjugated to BSA, applied by striping (1 μl/cm, target OD 3.5). The third stripe (23) is 17 mm downstream of area (45) and consists of goat anti-mouse antibody (Jackson Immunoresearch Labs Inc., Product Code 115-005-062), applied by striping (1 μl/cm of 1.5 mg/ml antibody). The device thus has excess free label.

Figure 3:
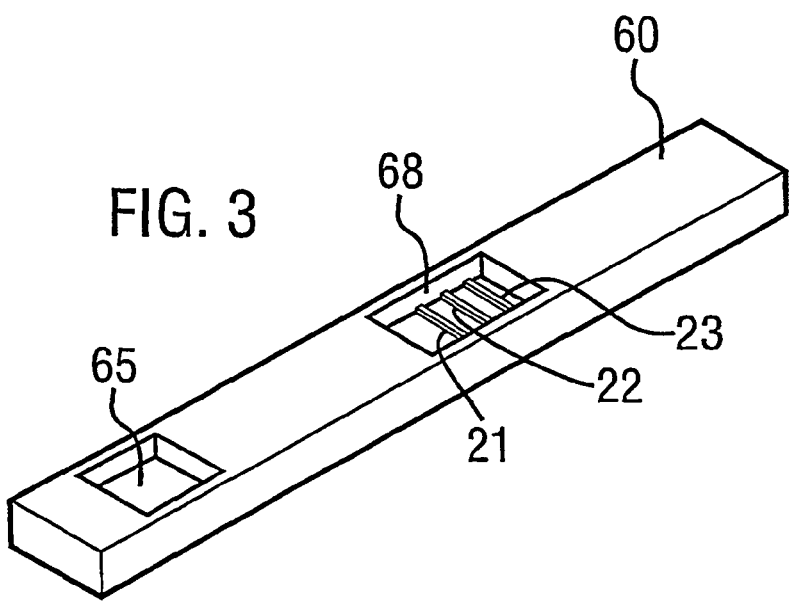
FIG. 3 shows the same when placed in a housing.

The assembled strip (1) was mounted in a plastic housing (60; Advanced Microdevices 8 mm cassette) having a window (65) through which a urine sample can be applied to absorbent paper (50) and a window (68) through which stripes (21), (22) and (23) are visible (FIGS. 1 and 3).

During use of this device, therefore, a urine sample is applied to absorbent paper (50). Lateral flow along the device (10) commences and the sample passes into pad (40) and through area (45), where any FSH in the sample binds to anti-FSH. Flow continues into nitrocellulose strip (20). At stripe (21), FSH-antibody complex is retained, but free antibody continues to stripe (23), where it is bound and retained.

During initial design, the device (10) did not include stripe (22). Day 3 first morning urine samples from patients with a serum FSH level of 10 mIU/ml were applied to devices and the colour intensity of stripe (21) was noted. This colour intensity is replicated in stripe (22). During use, therefore, a comparison of the colour intensity at stripes (21) and (22) indicates the level of FSH in the urine sample relative to the 10 mIU/ml standard—if the intensity of stripe (21) is greater than or equal to the intensity of stripe (22), the result is regarded as positive i.e. a urine FSH concentration corresponding to a serum FSH level of 10 mIU/L or greater.

Using the Device

For over 100 patients, a first morning urine sample and a blood sample were obtained on day 3 of the menstrual cycle. FSH levels in the blood samples were measured using the Abbott Imx™ or the Chiron ACS180 assays and the urine samples (160 μl) were applied to the device described above. The urine test strip results were read after 20 minutes in a 'blind' manner i.e. without knowledge of the results of the serum assays.

The results of the urine and serum tests are presented in the following table, in which patients have been sorted into ascending order based on serum FSH levels:

| Patient ID | Serum FSH (mIU/mL) | Urine Result |
|---|---|---|
| B12804 | 1.2 | − |
| B31304 | 1.5 | − |
| B12305 | 1.7 | − |
| P13 | 2.0 | − |
| B30404 | 2.0 | − |
| B52305 | 2.0 | − |
| B1205 | 2.1 | − |
| P7 | 2.3 | − |
| B13005 | 2.3 | − |
| B42303 | 2.4 | − |
| B11605 | 2.8 | − |
| S25 | 3.2 | − |
| P2 | 3.2 | − |
| B41704 | 3.3 | − |
| B51605 | 3.4 | − |
| I2305 | 3.4 | − |
| S17 | 3.5 | − |
| B22303 | 3.5 | − |
| B42305 | 3.6 | − |
| P11 | 3.9 | − |
| A1305 | 3.9 | − |
| B41104 | 4.0 | − |
| B0106 | 4.0 | − |
| B30405 | 4.1 | − |
| B40905 | 4.1 | − |
| G1205 | 4.2 | − |
| G0906 | 4.3 | − |
| I0905 | 4.3 | + |
| H2605 | 4.4 | − |
| B41605 | 4.5 | − |
| E1905 | 4.5 | − |
| I2905 | 4.5 | − |
| B11304 | 4.6 | − |
| H1206 | 4.6 | − |
| S30 | 4.7 | − |
| B21904 | 4.7 | − |
| B2605 | 4.8 | − |
| B13003 | 4.9 | − |
| B21805 | 5.1 | − |
| B40205 | 5.1 | − |
| A0806 | 5.1 | − |
| B1905 | 5.2 | − |
| B21304 | 5.4 | − |
| P5 | 5.7 | − |
| B11904 | 5.7 | − |
| S15 | 5.8 | − |
| B31904 | 5.9 | + |
| H0206 | 5.9 | − |
| S38 | 6.0 | − |
| B22505 | 6.0 | − |
| B50905 | 6.0 | − |
| B10905 | 6.1 | − |
| B42504 | 6.1 | − |
| B52504 | 6.1 | − |
| A1905 | 6.1 | + |
| B11104 | 6.2 | − |
| B50205 | 6.2 | − |
| I0406 | 6.2 | − |
| S23 | 6.3 | − |
| S28 | 6.3 | − |
| B21105 | 6.4 | + |
| B22804 | 6.5 | − |
| B43005 | 6.5 | − |
| B20405 | 6.6 | − |
| P9 | 6.8 | + |
| B20606 | 6.8 | − |
| B51104 | 6.8 | − |
| P17 | 6.9 | − |
| B30205 | 6.9 | − |
| B50404 | 7.1 | − |
| G0206 | 7.1 | − |
| B51306 | 7.2 | − |
| P19 | 7.4 | − |
| B51704 | 7.4 | − |
| B20404 | 7.5 | − |
| S21 | 7.6 | − |
| I1605 | 7.6 | − |
| B43003 | 7.7 | − |
| S34 | 7.9 | − |
| S12b | 8.1 | − |
| S36 | 8.2 | + |
| S32 | 8.3 | − |
| B52803 | 8.4 | − |
| G1905 | 8.7 | + |
| B32803 | 8.9 | − |
| G2605 | 9.6 | − |
| E1205 | 9.8 | − |
| H1205 | 9.9 | − |
| B71104 | 10.0 | + |
| E0906 | 10.1 | + |
| A0206 | 11.4 | + |
| S11b | 12.6 | + |
| P15 | 13.6 | + |
| E2605 | 14.4 | + |
| E0206 | 15.8 | + |
| S19 | 16.5 | + |
| A2505 | 32.1 | + |
| J1505 | 42.5 | + |
| J1206 | 43.2 | + |
| J0606 | 44.5 | + |
| K1505 | 49.9 | + |
| C0905 | 54.3 | + |
| F1105 | 54.3 | + |
| F1805 | 57.2 | + |
| K1305 | 58.6 | + |
| K2205 | 60.5 | + |
| D2605 | 60.8 | + |
| F1406 | 60.8 | + |
| C1605 | 65.0 | + |
| D1905 | 65.0 | + |
| C2305 | 66.9 | + |
| C2905 | 72.4 | + |
| C1306 | 72.6 | + |
| D1205 | 78.9 | + |
| D0106 | 84.5 | + |
| K3005 | 91.3 | + |
| K0506 | 95.3 | + |
| B93005 | 99.9 | + |
| B92305 | 102.5 | + |
| B91105 | 103.5 | + |
| B92804 | 109.8 | + |
| B90405 | 112.9 | + |
| D1306 | 117.0 | + |
| B82504 | 127.5 | + |

The results obtained using the urine test strip are particularly impressive. No false negatives were detected (i.e. where serum FSH levels were $\geq 10$ mIU/ml, the test strip always gave a positive result) and the level of false positives was very low—where serum FSH levels were <10 mIU/ml, only 7/88 positive results (8%) were given. Significantly, urine samples corresponding to serum FSH levels of 9.9 mIU/ml and 10 mIU/ml could be distinguished.

The device of the invention therefore shows 100% sensitivity, 92% specificity and 94.4% accuracy.

It will be understood that the invention has been described by way of example only and modifications may be made whilst remaining within the scope and spirit of the invention.

The invention claimed is:

1. A lateral flow device for indirectly determining a threshold concentration of serum Follicle Stimulating Hormone (FSH) in a subject by measuring FSH in a urine sample comprising:
   (a) an application zone for receiving a urine sample;
   (b) a labelling zone containing labeled binding partner for the FSH;

(c) a detection zone having an immobilized capture reagent for the FSH; and (d) a reference zone having a signal of fixed intensity indicative of the threshold concentration of serum FSH, wherein when the signal in the detection zone is less intense than the signal in the reference zone, the subject has a serum FSH level less than the threshold concentration; and when the signal in the detection zone is more intense than the signal in the reference zone, the subject has a serum FSH level more than the threshold concentration;

wherein the threshold concentration in serum is between 5mIU/ml and 20 mIU/ml.

2. The device of claim 1, wherein the threshold concentration in serum is 10 mIU/ml FSH.

3. The device of claim 1, wherein the labeled binding partner for the FSH is a tagged antibody.

4. The device of claim 3, wherein the antibody is tagged with colloidal gold.

5. The device of claim 1, wherein the immobilized capture reagent for the FSH is an antibody.

6. The device of claim 1, wherein the device has a control zone downstream of the detection zone which retains the labeled binding partner for the FSH which passes through the detection zone.

7. The device of claim 6, wherein the control zone and the reference zone are the same zone.

8. The device of claim 3, wherein the antibody which is used is a monoclonal antibody.

9. The device of claim 1, wherein the threshold concentration in serum is between 8mIU/ml FSH and 12 mIU/ml FSH.

10. The device of claim 5, wherein the antibody which is used is a monoclonal antibody.

11. A method for measuring serum FSH levels, comprising the steps of: (a) obtaining a urine sample from a subject; (b) applying the urine sample to the application zone of the lateral flow device according to claim 1; (c) detecting a signal in the detection zone of the lateral flow device; and (d) comparing the signal detected in step (c) with the signal in the reference zone, wherein when the signal in the detection zone is less intense than the signal in the reference zone, the subject has a serum FSH level less than the threshold concentration; and when the signal in the detection zone is equal to or more intense than the signal in the reference zone, the subject has a serum FSH level equal to or more than the threshold concentration, wherein said threshold concentration in serum is between 5mIU/ml and 20mIU/ml.

12. The method of claim 11, wherein the threshold concentration in serum is 10 mIU/ml FSH.

13. The method of claim 11, wherein the urine sample is obtained on day 3+/−1 of the menstrual cycle.

14. The method of claim 11, wherein the urine sample is a first morning urine sample.

15. The method of claim 11, wherein the threshold concentration in serum is between 8mIU/ml FSH and 12 mIU/ml FSH.

16. A method for measuring ovarian reserve, comprising the steps of: (a) obtaining a urine sample from a subject; (b) applying the urine sample to the application zone of the lateral flow device according to claim 1; (c) detecting a signal in the detection zone of the lateral flow device; and (d) comparing the signal detected in step (c) with the signal in the reference zone, wherein when the signal in the detection zone is less intense than the signal in the reference zone, the subject has normal ovarian reserve; and when the signal in the detection zone is equal to or more intense than the signal in the reference zone, the subject has diminished ovarian reserve, wherein said threshold concentration in serum is between 5mIU/ml and 20mIU/ml.

17. The method of claim 16, wherein the threshold concentration in serum is 10 mIU/ml FSH.

18. The method of claim 16, wherein the urine sample is obtained on day 3+/−1 of the menstrual cycle.

19. The method of claim 16, wherein the urine sample is a first morning urine sample.

20. The method of claim 16, wherein the threshold concentration in serum is between 8mIU/ml FSH and 12mIU/ml FSH.

* * * * *